(12) United States Patent
Hamano et al.

(10) Patent No.: US 6,585,768 B2
(45) Date of Patent: *Jul. 1, 2003

(54) INTRAOCULAR LENSES AND PROCESS FOR THE PRODUCING MOLDED-IN TYPE INTRAOCULAR LENSES

(75) Inventors: Migio Hamano, Tokyo (JP); Akihiko Shibuya, Tokyo (JP); Takuji Yamaya, Tokyo (JP)

(73) Assignee: Hoya Healthcare Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,848

(22) PCT Filed: Nov. 30, 1998

(86) PCT No.: PCT/JP98/05370
§ 371 (c)(1),
(2), (4) Date: Jul. 20, 1999

(87) PCT Pub. No.: WO99/27978
PCT Pub. Date: Jun. 10, 1999

(65) Prior Publication Data
US 2002/0188352 A1 Dec. 12, 2002

(30) Foreign Application Priority Data
Dec. 2, 1997 (JP) .............................. 9-332009
Dec. 12, 1997 (JP) ............................. 9-343005

(51) Int. Cl.[7] ................................................. A61F 2/16
(52) U.S. Cl. ...................... 623/6.37; 623/6.56; 523/106
(58) Field of Search ............................ 623/6.56, 5.16, 623/924, 926, 6.37, 6.39, 6.42, 6.49, 6.54; 523/106, 107; 351/160 H; 424/427

(56) References Cited

U.S. PATENT DOCUMENTS

| 4,542,540 A | | 9/1985 | White |
| 4,790,846 A | * | 12/1988 | Christ et al. .................. 623/6 |
| 4,790,847 A | * | 12/1988 | Woods ........................... 623/6 |
| 5,217,491 A | | 6/1993 | Vanderbilt |
| 5,264,465 A | * | 11/1993 | Futamura et al. ........... 523/106 |
| 5,300,117 A | | 4/1994 | Baikoff et al. |
| 5,326,506 A | | 7/1994 | Vanderbilt |
| 5,476,512 A | * | 12/1995 | Sarfarazi ....................... 623/6 |
| 5,713,958 A | | 2/1998 | Weiser |
| 5,814,680 A | * | 9/1998 | Imafuku et al. ............ 523/106 |

FOREIGN PATENT DOCUMENTS

| JP | 60-75054 | 4/1985 |
| JP | 61-90656 | 5/1986 |
| JP | 62-142558 | 6/1987 |
| JP | 62-152450 | 7/1987 |
| JP | 1-158949 | 6/1989 |
| JP | 4-292609 | 10/1992 |
| JP | 4-295353 | 10/1992 |
| JP | 5-269191 | 10/1993 |
| JP | 6-78941 | 3/1994 |
| JP | 6-78942 | 3/1994 |
| JP | 9-19446 | 1/1997 |
| JP | 10-85319 | 4/1998 |

* cited by examiner

Primary Examiner—Paul B. Prebilic
(74) Attorney, Agent, or Firm—Nixon & Vanderhye P.C.

(57) ABSTRACT

A one-piece intraocular lens having an optic portion and a haptic portion, the optic portion being formed of a copolymer obtained by copolymerization of predetermined amounts of 2-[2-(perfluorooctyl)ethoxy]-1-methylethyl (meth)acrylate, 2-phenylethyl (meth)acrylate, alkyl (meth)acrylate and a crosslinking monomer, the haptic portion being formed of polymethyl methacrylate, a process for the production thereof, and a soft intraocular lens having an optic portion and a haptic portion formed of a soft material, the haptic portion having a bendable portion having specific functions, the one-piece intraocular lens being insertable into an eye through a small incision with the optic portion being bent, the soft intraocular lens permitting the prevention of the deformation of the soft optic portion caused by the shrink of a capsule when the soft intraocular lens is inserted into an eye.

26 Claims, 7 Drawing Sheets

OPTICAL AXIS DIRECTION

INTRAOCULAR LENSES AND PROCESS FOR THE PRODUCING MOLDED-IN TYPE INTRAOCULAR LENSES

This application is 35 U.S.C. § 371 of PCT/JP98/05370, filed Nov. 30, 1998

FIELD OF THE INVENTION

The present invention relates to an intraocular lens and a process for the production of a one-piece intraocular lens. More specifically, the present invention particularly relates to a one-piece intraocular lens which can be inserted through a small incision by bending its optic portion when it is inserted into an eye, a process for the efficient production of the same, and a soft intraocular lens which permits the prevention of deformation of a soft optic portion caused by the shrink of a capsule after intraocularly inserted.

TECHNICAL BACKGROUND

In recent years, with an increase in the population of aged people, senile cataract patients are distinctively increasing. A treatment against cataract is carried out by removing a clouded nucleus and cortex of a crystalline lens and either correcting a vision with an eyeglass or a contact lens or inserting an intraocular lens, while it is general practice to employ a method in which a crystalline lens as a whole is removed and an intraocular lens is fixed.

The above intraocular lens comprises an optic portion which functions as a substitute lens for the crystalline lens removed due to cataract and a narrow and long filament-like haptic portion which is to fix and hold the optic portion in the central position in a capsule. It is known that the above intraocular lens includes an intraocular lens of a type which is formed by separately producing the haptic and optic portions and later combining them (sometimes called two-piece or three-piece type), and a one-piece intraocular lens formed by integrally producing the haptic and optic portions (sometimes called one-piece type). As a material for the optic portion, there has been mainly used polymethyl methacrylate (to be referred to as "PMMA" hereinafter) which is a hard material. The reason for the use of PMMA as a material for the above planting intraocular lens is that it is transparent and excellent in stability in organisms (biocompatibility) and that it has adequate machinability and can provide elaborate lenses stably. As a material for the hepatic portion for holding the above optic portion formed of PMMA, for example, a mono-filament of PMMA, polypropylene or polyimide has been used. Concerning the bonding of the above optical portion and haptic portion, as one type, a small hole for attaching the haptic portion is made in the optic portion, the haptic portion is inserted in the small hole after the optic portion is completed, then the haptic portion is fixed to the optic portion by staking or laser (two-piece or three piece type), or there is a one-piece type integrally formed of PMMA.

On the other hand, with a widened use of an ultrasonic emulsification aspiration method in recent years, there has been developed an intraocular lens which can be inserted through a small incision, for decreasing postoperative astigmatism and an operation stress. That is, the above intraocular lens is formed of a soft material as a material for the optic portion so that it can be bent so as to be inserted through a small incision.

Since, however, the soft material is difficult to machine, i.e., cut and polish unlike a conventional PMMA, the production of the optic portion generally uses a cast-molding method in which a monomer, a prepolymer or an oligomer as a material for forming the optic portion is polymerized in a mold. Further, since it is also difficult to mechanically make a small hole in the method of attaching the haptic portion, it is required to employ a method different from the conventional method.

For producing the above soft intraocular lens, various method, for example, shown below have been so far proposed.

(1) A method of producing an intraocular lens having an easily-non-removable haptic portion, in which the end portion of a filament constituting the haptic portion is permanently deformed to form a mechanical engagement portion having the form of a bulb, etc., or another filament having a mechanical engagement portion is bonded to the end of the former filament to form a terminal portion of the haptic portion and an optical member is mold-shaped with the terminal portion inserted (JP-A-62-142558, JP-A-62-152450).

(2) A method of producing an intraocular lens, in which a soft optical material is polymerized in a mold, then, a mold with a polymerized soft optical material in it is cooled to harden the soft material, a small hole in which a haptic portion is to be inserted and a small hole in which an anchor filament is to be inserted are mechanically made in the optic portion, then, the haptic portion is inserted in the haptic-portion-inserting small hole, a filament formed of the same material as that of the haptic portion is inserted in the anchor-filament-inserting small hole, an intersection of the haptic portion and the anchor filament is irradiated with a laser beam to fuse the haptic portion to the hole, and further, irradiation with a laser beam is effected along the inserting holes (JP-A-4-292609).

(3) A method of producing a foldable intraocular lens, in which a rod of a homopolymer or a copolymer of 2-hydroxyethyl methacrylate (HEMA) was prepared as a foldable optical member, the rod is placed in a tubular mold, a haptic portion is formed around the rod by polymerizing a hard material such as PMMA, then, a disc is obtained by cutting the rod, ground and polished to produce an intraocular lens and the lens is hydrated (allowed to contain water) (JP-A-4-295353).

(4) A method in which a flat plate is prepared from a crosslinked acrylic resin material, placed on a holder and cut into a disc with a lathe at a low temperature, the disc is cut to form a soft optic portion and then the soft optic portion is provided with haptic portions to obtain a three-piece type intraocular lens, or the above flat plate is cut into a material in the form of a lens to obtain an intraocular lens having a foldable optic portion and a soft haptic portion formed of the same soft material as the material of the optic portion (JP-A-1-158949).

(5) A method of producing an intraocular lens, in which an optical material having a diameter of 5 mm and a height of 20 mm was prepared by polymerization and then placed in the center of a cylinder having an inner diameter of 15 mm and a height of 20 mm, a monomer for forming a material of a haptic portion is polymerized in a circumferential portion thereof, and then, a material in the form of an intraocular lens is prepared by cutting and immersed in an alcohol for about 48 hours to soften the optic portion by esterification (JP-A-5-269191).

However, the above methods of producing intraocular lenses all have defects that the procedures are complicated and that the production efficiency is poor. That is, in the above method (1), it is required to make a plastic filament which is to form the haptic portion into a complicated form. The filament which is to form the haptic portion has a diameter of approximately 0.15 mm, and it is required to provide an extremely complicated and fine step for making the end portions of all the filaments in one form by melting the under heat. The haptic portion is required to have a form suitable for holding and fixing in an eye, and the form thereof is elaborately made by thermoforming. That is, when a soft optical material is produced in a mold so as to surround the above elaborately made haptic portion, the haptic portion is again exposed to heating and pressing steps, and the form and dimensions thereof may be altered.

In the above method (2), it is required to cool the material and make two holes, the hole for inserting the haptic portion and the anchor-filament-inserting hole which intersects with the former hole, and it is also required to insert the haptic portion and the anchor filament in the holes and attain the fusing of the haptic portion and the filling the hole with filament by repeatedly irradiating them with laser beam. Therefore, considerably complicated procedures are required.

In the above method (3), the optic portion is formed of a material composed mainly of HEMA, and a lens at the time of cutting is hard, but it is made soft by hydration after the cutting. HEMA shows a difference in water absorptivity from one lot to another, and it is difficult to maintain constant performances of intraocular lenss. Further, it takes a time during an operation to hydrate the intraocular lens, and further, when an intraocular lens is hydrated in advance, it is difficult to the intraocular lens in a sterile state.

Further, in the above method (4), the material of the haptic portion is the same as the material of the optic portion, and the haptic portion is therefore soft. The haptic portion of a conventional intraocular lens has a diameter of approximately 0.1 to 0.2 mm, and the haptic portion is considerably soft. It is therefore thought that maintaining an haptic portion angle is difficult and that the positional stability of the optic portion in a capsule is difficult.

In the above method (5), no haptic portion material having reactivity with an alcohol can be used. It is therefore not possible to use PMMA which is generally used at present.

Further, a chemical reaction is caused on the optic portion after the form of an intraocular lens is made by precision cutting and polishing, and the form of the optic portion (change in curvature, thickness, optical radius, etc.) may be changed, and it is difficult to maintain the haptic portion angle during processing.

Meanwhile, when the optic portion and the haptic portion are bonded in a two-piece or three-piece intraocular lens, an angle is provided in quite a few cases such that the haptic portion forms an angle of approximately 5 to 10 degrees with a plane at right angles with the optical axis of the optic portion. The above is for stable registering after the lens is fitted in a capsule.

Figure 7:
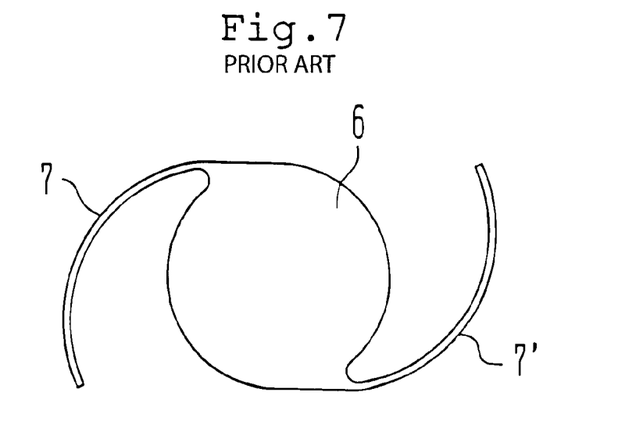
FIG. 7 is a plan view of one conventional intraocular lens.
Figure 8:
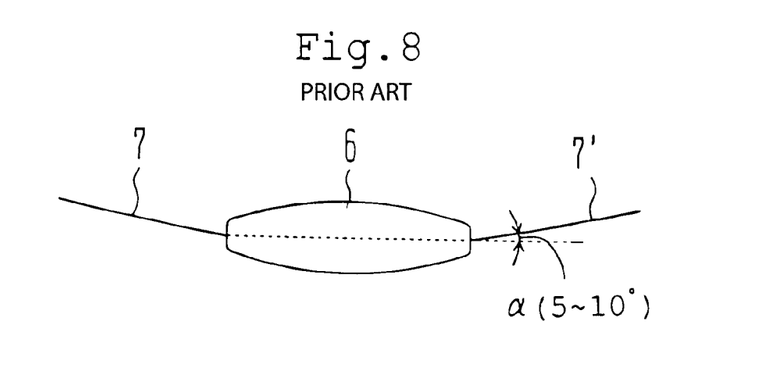
FIG. 8 is a schematic side view of a conventional one-piece intraocular lens.

Further, in the above one-piece type intraocular lens, the optic portion and the haptic portion are integrally formed in many cases. FIG. 7 shows a plan view of a conventional one-piece intraocular lens. FIG. 8 schematically shows a side view of the haptic portion of a conventional one-piece intraocular lens. In these Figures, numeral 6 indicates the optic portion, and numeral 7, 7' is the haptic portion. In the form of the haptic portion of a one-piece type intraocular lens, an angle of approximately 5 to 10 degrees is provided in many cases as shown in FIG. 8, like the above two-piece or three-piece type intraocular lens.

Further, as far as the form of the haptic portion is concerned, there is an intraocular lens called a wing type.

Figure 9:
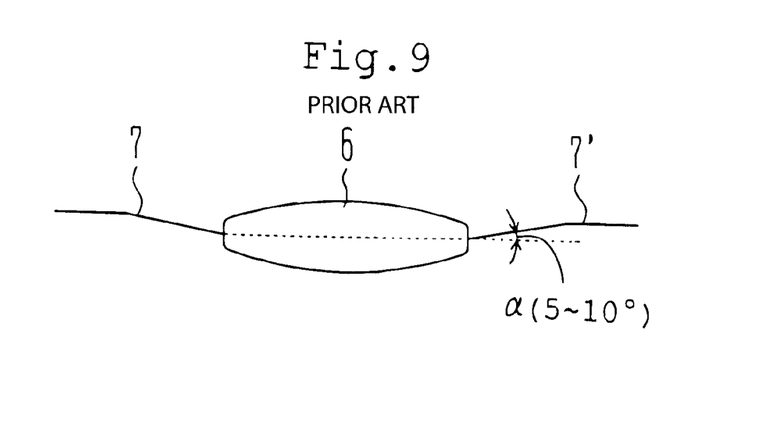
FIG. 9 is a schematic side view of a wing type intraocular lens.

FIG. 9 schematically shows a side view of an wing type intraocular lens. The haptic portion 7,7' rises at an angle of approximately 5 to 10 degrees and then comes to be parallel with a plane at right angles with the optical axis of the optic portion. Intraocular lenses of all the types are designed such that the lenses inserted in capsules can be stably fixed in the capsules.

Further, it is known that the haptic portion of the above soft intraocular lens is also designed as a type provided with an angle of approximately 5 to 10 degrees or as a wing type.

Meanwhile, when an intraocular lens is inserted in a capsule, the inner diameter of the capsule shrinks to approximately 10 mm, and the haptic portion is accordingly compressed. Generally, the optic portion is supported by the function of the elastic force generated by the above compression of the haptic portion. In this case, part of the elastic force is transmitted to the optic portion. When the optic portion is formed of a hard material such as PMMA, almost no problem is caused by the transmission of the above elastic force. However, when the optic portion is formed of a soft material, depending upon how an intraocular lens is inserted in a capsule, the optic portion may be deformed or distorted, or the displacement of a lens may not be constant, due to the above elastic force transmitted to the optic portion, so that the resolution and lens strength may not be attained as designed.

DISCLOSURE OF THE INVENTION

Under the circumstances, it is a first object of the present invention to provide a one-piece type intraocular lens having an optic portion having an elasticity sufficient to be bent when the intraocular lens is inserted in an eye and a haptic portion which is like a haptic portion used in a conventional intraocular lens formed of PMMA and is for holding and fixing the optic portion in the eye and which is not easily removable.

Further, it is a second object of the present invention to provide a process for efficiently producing the above one-piece type intraocular lens free of a variability in product quality without requiring any complicated steps.

Further, it is a third object of the present invention to provide a soft intraocular lens whose optic portion is deformed or distorted in almost no case when the haptic portion thereof is compressed due to the shrink of a capsule after the soft intraocular lens is inserted in the capsule.

The term "haptic portion" in the present specification refers to a plurality of members extending from the optic portion as shown, e.g., in FIG. 4, and is used in this sense throughout the specification.

The present inventors have made diligent studies to achieve the above objects, and have found that the above first object can be achieved by a one-piece type lens having an optic portion and a haptic portion, said optic portion being formed of a copolymer obtained by polymerization of a monomer mixtures containing 2-[2-(perfluorooctyl)ethoxy]-1-methylethyl (meth)acrylate, 2-phenylethyl (meth)acrylate, alkyl (meth)acrylate of which the alkyl group has a specific number of carbon atoms and a crosslinking monomer in a predetermined amount ratio and said haptic portion being formed of PMMA.

It has been also found that the above second object can be achieved as follows.

The above one-piece type lens can be easily and efficiently produced without a variability in product quality by polymerizing the above optic-portion-forming monomer mixture with keeping the monomer mixture in contact with a haptic-portion-forming material containing PMMA, or polymerizing a haptic-portion-forming monomer containing methyl methacrylate with keeping the haptic-portion-forming monomer in contact with an optic-portion-forming material formed of a copolymer obtained by polymerization of the above monomer mixture, to integrate the optic-portion-forming material and the haptic-portion-forming material, and cutting and polishing the integrated product.

Further, it has been found that the above third object can be achieved by a soft intraocular lens whose haptic portion is provided with a bendable portion which can absorb at least part of an external compressive force exerted on the haptic portion by deformation so that the bendable portion can decrease the force to be transmitted to the optic portion.

The present invention has been completed on the basis of the above findings.

That is, according to the present invention, there is provided a one-piece intraocular lens having an optic portion which functions as a substitute lens for a crystalline lens and a haptic portion for fixing and holding the optic portion in a predetermined position in an eye, the optic portion being formed of a copolymer obtained by polymerization of a monomer mixture containing

(a) 5 to 20% by weight of 2-[2-(perfluorooctyl)ethoxy]-1-methylethyl (meth)acrylate of the formula (I), (I)

wherein $R^1$ is hydrogen or methyl,

(b) 40 to 70% by weight of 2-phenylethyl (meth)acrylate of the formula (II), (II)

wherein $R^2$ is hydrogen or methyl, (c) 25 to 50% by weight of alkyl (meth)acrylate of the formula (III), (III)

wherein $R^3$ is hydrogen or methyl and $R^4$ is a $C_4$–$C_{12}$ linear, branched or cyclic alkyl group, and (d) 0.5 to 5% by weight, based on the total amount of the components (a) to (c), of a crosslinking monomer, the haptic portion being formed of polymethyl methacrylate (the above intraocular lens will be sometime referred to as "intraocular lens 1" hereinafter).

According to the present invention, further, there is provided a process for the production of a one-piece intraocular lens having an optic portion which functions as a substitute lens for a crystalline lens and a haptic portion for fixing and holding the optic portion in a predetermined position in an eye, the process comprising polymerizing an optic-portion-forming monomer mixture containing 5 to 20% by weight of 2-[2-(perfluorooctyl)ethoxy]-1-methylethyl (meth)acrylate of the above formula (I), (b) 40 to 70% by weight of 2-phenylethyl (meth)acrylate of the above formula (II), (c) 25 to 50% by weight of alkyl (meth)acrylate of the above formula (III) and (d) 0.5 to 5% by weight, based on the total amount of the components (a) to (c), of a crosslinking monomer, with keeping the monomer mixture in contact with a haptic-portion-forming material containing polymethyl methacrylate, or polymerizing a haptic-portion-forming monomer containing methyl methacrylate with keeping the haptic-portion-forming monomer in contact with an optic-portion-forming material formed of a copolymer obtained by polymerization of the above monomer mixture, to integrate the optic-portion-forming material and the haptic-portion-forming material, and cutting and polishing the integrated product.

Further, according to the present invention, there is provided a soft intraocular lens having an optic portion formed of a deformable soft material which functions as a substitute lens for a crystalline lens and a haptic portion which is formed of arm-like two members extending outwardly from circumferential portions of the optic portion and is for fixing and holding the optic portion in a predetermined position in an eye, the haptic portion being provided with a bendable portion which, when a compressive force is externally exerted on the haptic portion so as to move at least any site of the haptic portion toward the optic portion, can absorb at least part of the external compressive force by deformation and decreases the force to be transmitted to the optic portion (the above soft intraocular lens will be sometimes referred to as "intraocular lens 2" hereinafter).

In the present invention, the term "(meth)acrylate" includes acrylate and methacrylate.

BEST MODES FOR PRACTICING THE INVENTION

The one-piece intraocular lens (intraocular lens 1) of the present invention has an optic portion which functions as a substitute lens for a crystalline lens and a haptic portion for fixing and holding the optic portion in a predetermined position in an eye.

The above optic portion is formed of a copolymer obtained by copolymerization of a monomer mixture containing the following components (a) to (d). Component (a), i.e., 2-[2-(perfluorooctyl)ethoxy]-1-methylethyl (meth) acrylate of the formula (I), is an essential component for decreasing the surface sticking nature of the optic portion of the intraocular lens and imparting the intraocular lens with the function that the intraocular lens can restore its original shape in a proper time period of approximately 20 to 60 seconds to stabilize itself.

In the formula (1), $R^1$ is hydrogen or methyl, while $R^1$ is preferably methyl.

Component (b), i.e., of 2-phenylethyl (meth)acrylate of the formula (II), is a component for imparting the optic portion of the intraocular lens with a high refractive index.

In the formula (2), $R^2$ is hydrogen or methyl, while $R^2$ is preferably methyl.

Component (c), i.e., alkyl (meth)acrylate of the formula (III), is a component for imparting the optic portion of the intraocular lens with high flexibility.

In the formula (III), $R^3$ is hydrogen or methyl, while $R^3$ is preferably hydrogen. $R^4$ is a $C_4$–$C_{12}$ linear, branched or cyclic alkyl group. Examples of the alkyl (meth)acrylate of the formula (III) preferably include n-butyl acrylate, isobutyl acrylate, isoamyl acrylate, n-hexyl acrylate, cyclohexyl acrylate, 2-ethylhexyl acrylate, n-octyl acrylate, isooctyl acrylate and decyl acrylate, isodecyl acrylate. These acrylates may be used alone or in combination.

Component (d), i.e., a crosslinking monomer, is a component for preventing the deformation of the optic-portion-forming material during the polymerization and improving the optic portion of the intraocular lens in mechanical strength.

Examples of the above crosslinking monomer include ethylene glycol dimethacrylate (to be referred to as "EDMA" hereinafter), diethylene glycol dimethacrylate, triethylene glycol dimethacrylate, tetraethylene glycol dimethacrylate, 1,4-butanediol dimethacrylate, 1,4-butanediol diacrylate and 1,6-hexanediol dimethacrylate. These monomers may be used alone or in combination.

In the present invention, the content of each component in the monomer mixture is as follows. On the basis of the total amount of components (a) to (c), the content of component (a) is 5 to 20% by weight, the content of component (b) is 40 to 70% by weight, and the content of component (c) is 25 to 50% by weight. When the content of component (a) is less than 5% by weight, there may be no sufficient effect on decreasing the surface sticking nature of the optic portion of the intraocular lens and imparting the intraocular lens with the function that the intraocular lens can restore its original shape in a proper time period, e.g., of approximately 20 to 60 seconds to be stabilized. When it exceeds 20% by weight, the capability of restoring the shape of the optic portion tends to be decreased. In view of an effect on decreasing the surface sticking nature and the shape restoring capability, the content of component (a) is preferably 7 to 15% by weight.

When the content of component (b) is less than 40% by weight, it is difficult to impart the optic portion of the intraocular lens with an adequate refractive index. When it exceeds 70% by weight, the optic portion comes to show decreased flexibility and is hard to be bent into a small size. In view of the refractive index and flexibility of the optic portion, the content of component (B) is preferably 42 to 63% by weight.

When the content of component (c) is less than 25% by weight, it is difficult to impart the optic portion of the intraocular lens with sufficient flexibility. When it exceeds 50% by weight, the surface sticking nature of the optic portion may increase. In view of the flexibility and the surface sticking nature of the optic portion, the content of the component (c) is preferably 30 to 46% by weight.

On the other hand, the content of the crosslinking monomer as component (d) is 0.5 to 5% by weight based on the total amount of the above components (a) to (c). When the content of component (d) is less than 0.5% by weight, the effect of use of the crosslinking monomer is not sufficiently produced. When it exceeds 5% by weight, the number of crosslinkage points increases to excess so that the optic portion is fragile and that the mechanical strength of the optic portion may decrease. In view of the effect and the mechanical strength, the content of the crosslinking monomer is preferably 1 to 4% by weight.

In the present invention, the monomer mixture may contain a monomer capable of absorbing ultraviolet light as required.

The above monomer capable of absorbing ultraviolet light includes, for example, a compound of the formula (IV), (IV)

wherein X is hydrogen or chlorine and $R^5$ is hydrogen or methyl.

Specific example of the compound of the above formula (IV) include 5-chloro-2-[2-hydroxy-5-(β-methacryloyloxyethylcarbamoyloxyethyl)]phenyl-2H-benzotriazole (to be referred to as "CHMP" hereinafter) and 2-[2-hydroxy-5-(β-methacryloyloxyethylcarbamoyloxyethyl)]-phenyl-2-H-benzotriazole.

Further, as other ultraviolet absorbent monomer, there may be used 2-(2'-hydroxy-3'-tert-butyl-5'-methylphenyl)-5-(2'-methacryloyloxyethyl)benzotriazole of the following formula.

The content of the above monomer capable of absorbing ultraviolet light, based on the total amount of the components (a) to (c), is preferably 0.05 to 3% by weight, particularly preferably 0.1 to 2% by weight. When the above content is less than 0.05% by weight, no effect on the prevention of ultraviolet light can be expected. When it exceeds 3% by weight, the effect thereof is almost no further increased, or it is disadvantageous in view of an economic performance.

In the present invention, further, the above monomer mixture may contain a coloring monomer such as a polymerizable dyestuff as required for coloring the optic portion of the intraocular lens.

In the intraocular lens of the present invention, the optic portion which functions as a substitute lens for a crystalline lens is formed of a copolymer obtained by copolymerization of the above components (a) to (d) and optional components such as the above monomer capable of absorbing ultraviolet light and the above coloring monomer.

The above copolymer is produced by adding a polymerization initiator to the above monomer mixture, fully stirring the resultant mixture to prepare a homogeneous monomer mixture, and polymerizing the homogeneous mixture according to a general method. The above general method refers to a method in which a radical polymerization initiator is added, and then the mixture is temperature-increased stepwise or continuously from 40 to 120° C. or the mixture is irradiated with ultraviolet light or visible light.

Specifically, the above radical polymerization initiator can be selected from generally known radical polymerization initiators including azo-containing initiators such as azobisvaleronitrile and azobisisobutyronitrile (to be referred to as "AIBN" hereinafter) and organic peroxides such as bis(4-t-butylcyclohexyl)peroxydicarbonate. The amount of the above initiator based on the total monomer amount is preferably 0.1 to 5% by weight.

In the one-piece intraocular lens of the present invention, the haptic portion for fixing and holding the above optic portion in a predetermined position in an eye is formed of polymethyl methacrylate, and the haptic portion and the optic portion are required to be integrated.

Concerning the form of the above one-piece intraocular lens, there are known a lens of which the haptic portion form has a angle of approximately 5 to 10 degrees and a sp-called wing type lens of which the haptic portion rises at an angle of approximately 5 to 10 degrees and comes to be horizontal in an end portion thereof.

When one-piece intraocular lens have the above forms, the optic portion undergoes no deformation even when the haptic portion is compressed (after the intraocular lens is inserted) so long as the optic portion is formed of a hard material such as PMMA. Further, the positional stability of the optic portion in an eye is presumably excellent since the displacement of the optic portion is low when the haptic portion is compressed.

However, when the optic portion is soft like the intraocular lens of the present invention, the above type having an angle of approximately 5 to 10 degrees and the above wing type suffers the deformation of the optic portion and an increased displacement of the optic portion when the haptic portion is compressed. Therefore, the haptic portion preferably has the form of a hopper for removing the deformation of the optic portion and the displacement of the optic portion when the haptic portion is compressed. The above form of the hopper will be specifically explained with reference to drawings later.

The process for the production of the above one-piece intraocular lens is not specially limited so long as there can be obtained a one-piece intraocular lens having a structure in which the optic portion and the haptic portion are formed of the above-explained materials and integrated. However, when the following process of the present invention is employed, there can be highly efficiently produced intraocular lenses of which the haptic portion is not easily removable and which are free of a variability in product quality.

In the process of the present invention, (1) the optic-portion-forming monomer mixture is polymerized with keeping the monomer mixture in contact with a haptic-portion-forming material containing PMMA, to integrate the optic-portion-forming material and the haptic-portion-forming material, and then, the integrated product is cut and polished to obtain an intended one-piece intraocular lens, or (2) a haptic-portion-forming monomer containing methyl methacrylate is polymerized with keeping the haptic-portion-forming monomer in contact with an optic-portion-forming material formed of a copolymer obtained by polymerization of the above monomer mixture, to integrate the optic-portion-forming material and the haptic-portion-forming material, and then, the integrated product is cut and polished to obtain an intended one-piece intraocular lens.

According to the above process, an interpenetrating network (IPN) structure is formed in the junction of the optic-portion-forming material and the haptic-portion-forming material, and as a result, in the one-piece intraocular lens obtained as an end product, the haptic portion does not at all easily break away from the optic portion.

Since the optic-portion-forming material is soft, the cutting and polishing are preferably carried out with cooling. That is, it is preferred to carry out the cutting and polishing at a low-temperature atmosphere of approximately −10 to 0° C.

In the above processes (1) and (2), the process (1) is particularly preferred. For the process (1), for example, there is preferably employed a method in which a disc which is formed of PMMA and has a cylindrical concave portion having predetermined dimensions is provided, the above optic-portion-forming monomer mixture is charged into the concave portion, polymerized and then cut and polished with cooling, to produce an intended one-piece intraocular lens.

The process for the production of the one-piece intraocular lens will be specifically explained with reference to drawings hereinafter.

Figures 1A, 1B:
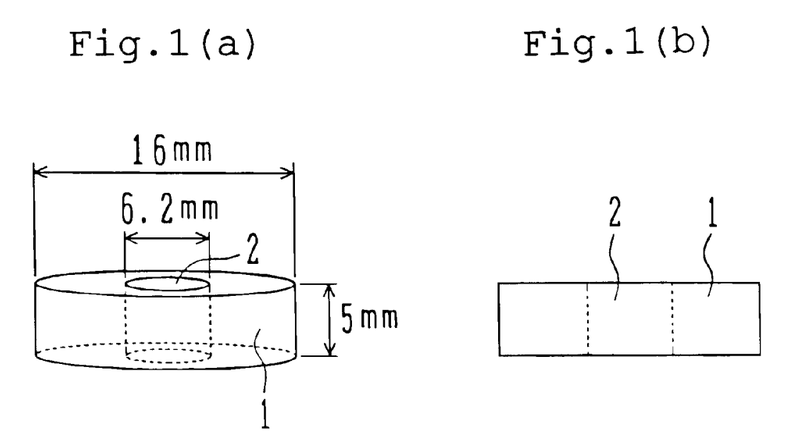
FIG. 1(a) is a perspective view of one example of a disc which is formed of PMMA and has a cylindrical concave portion.
FIG. 1(b) is a side view of the same.
Figures 2A, 2B:
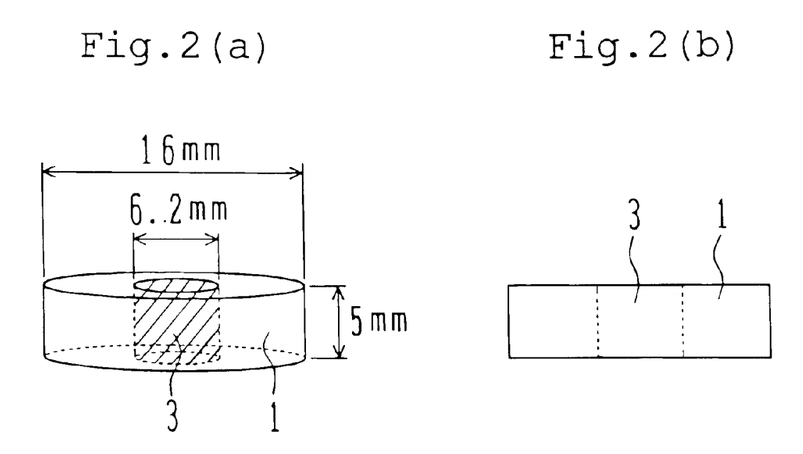
FIG. 2(a) is a perspective view showing a state where a monomer mixture for forming an optic portion is charged in the concave portion of the disc shown in FIG. 1.
FIG. 2(b) is a side view showing the same.
Figure 3:
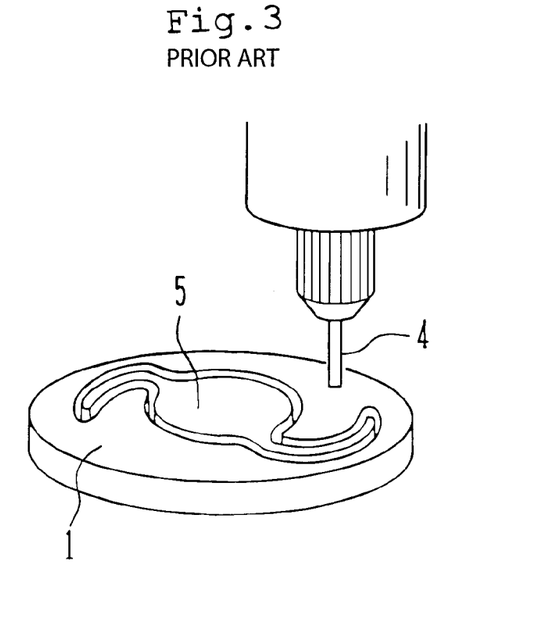
FIG. 3 is a perspective view for explaining the cutting of a material with a milling machine for a one-piece type intraocular lens.
Figures 4A, 4B:
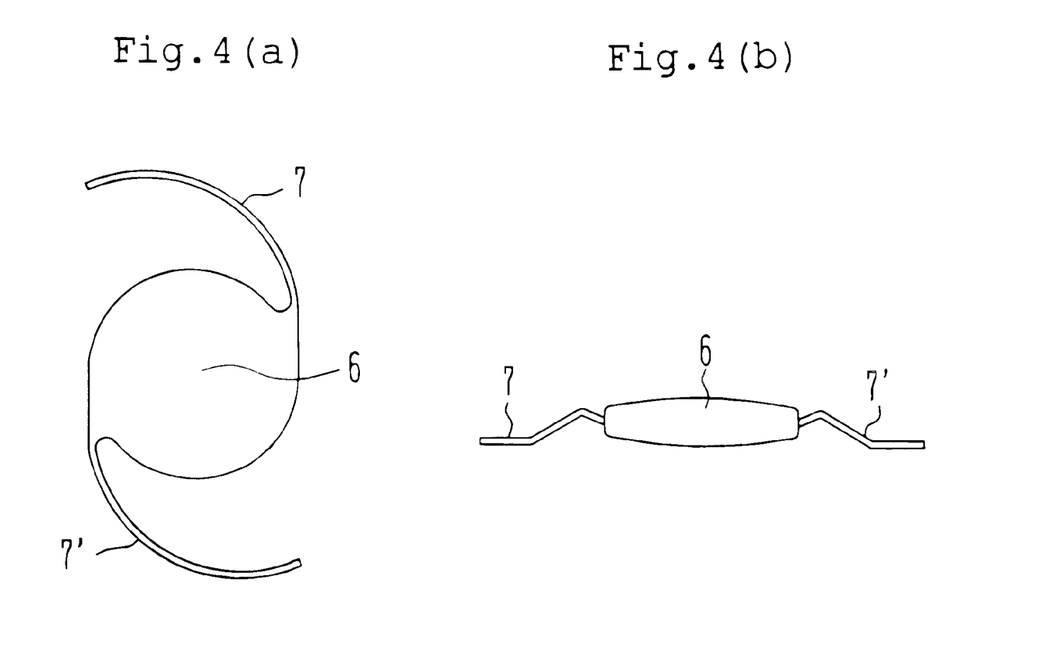
FIG. 4(a) is a front view of one example of the intraocular lens (intraocular lens 1) of the present invention.
FIG. 4(b) is a side view of the same.

FIG. 1(*a*) is a perspective view of one example of a disc which is formed of PMMA and has a cylindrical concave portion, and FIG. 1(*b*) is a side view of the same. FIG. 2(*a*) is a perspective view showing a state where the monomer mixture for forming the optic portion is charged in the concave portion of the disc shown in FIG. 1, and FIG. 2(*b*) is a side view showing the same. FIG. 3 is a perspective view for explaining the cutting of a material with a milling machine for a one-piece type intraocular lens. FIG. 4(*a*) is a front view of one example of the intraocular lens (intraocular lens 1) of the present invention, and FIG. 4(*b*) is a side view of the same.

First, a disc 1 which has a cylindrical concave portion 2 having a diameter of 6.2 mm, has a diameter of 16 mm and a thickness of approximately 5 mm as shown in FIG. 1 and is formed of PMMA is prepared. In FIG. 1, the cylindrical concave portion 2 has a diameter of 6.2 mm, while the form, diameter, etc., of the concave portion can be properly selected depending upon the form of the optic portion of an intended one-piece intraocular lens.

Further, the method of forming the above concave portion is not specially limited, and the concave portion can be formed by means of a milling machine. However, it is advantageous to employ a method in which a tool having a shape to be formed is prepared and the concave portion is formed in a disc by means of a press machine, since a complicated form can be easily produced. Further, the disc material is also pressed (stretched), so that the tensile strength, etc., are improved. As a result, the haptic portion can be improved in strength.

Then, as shown in FIG. 2, the above optic-portion-forming monomer mixture 3 is charged into the cylindrical concave portion of the disc 1 formed of PMMA, and the monomer mixture is polymerized by heating it approximately from 40° C. to 120° C. After the polymerization is completed, a disc having a thickness of 3 mm was taken by cutting, and with cooling, a base surface is cut. Then, with cooling, a material 5 for a lens having the optic portion and the haptic portion integrated is taken by cutting with a milling machine as shown in FIG. 3. Then, with cooling a surface opposite to the base-cut surface, the front surface is cut, and further, the lens is barrel-polished at a low temperature, whereby there can be obtained the one-piece intraocular lens of the present invention in which the optic portion 6 and the hopper-shaped haptic portion 7,7' are integrated as shown in FIG. 4.

The soft intraocular lens (intraocular lens 2) of the present invention will be explained hereinafter.

The soft intraocular lens (intraocular lens 2) of the present invention has an optic portion which is formed of a deformable soft material and functions as a substitute lens for a crystalline lens and a haptic portion which is formed of arm-like members extending outwardly from circumferential portions of the optic portion and is for fixing and holding the optic portion in a predetermined position in an eye. And, the haptic portion has a bendable portion which, when a compressive force is externally exerted on the haptic portion so as to move at least any site of the haptic portion toward the optic portion, can absorb at least part of the external compressive force by deformation and decreases the force to be transmitted to the optic portion.

The above bendable portion particularly preferably absorbs, by deformation, at least part of a force which is exerted on the haptic portion so as to move the optic portion in a direction in parallel with the optical axis of the optic portion.

Further, the soft intraocular lens preferably has a structure in which the above haptic portion is formed so as to form a first angle with a plane at right angles with the optical axis of the above optic portion as the haptic portion extends outwardly from its start portion in the vicinity of the above optic portion, and the above bendable portion has a first bendable portion which is bent so as to form a second angle, an angle opposite to the above first angle, with a plane at right angles with the optical axis of the optic portion in a position located outside the above start portion of the haptic portion and a second bendable portion which is bent so as to form a third angle, an angle opposite to the above second angle, with a plane at right angles with the optical axis of the above optic portion in a position located outside the first bendable portion.

In the soft intraocular lens (intraocular lens 2) having the above structure, the first angle is preferably 12 degrees or less, and the distance from the start portion of the haptic portion to the first bendable portion is preferably 3 mm or less.

The soft intraocular lens (intraocular lens 2) of the present invention is particularly preferably a one-piece intraocular lens of which the optic portion and the haptic portion are integrally formed. Further, the soft intraocular lens preferably has the haptic portion formed of a material having a higher hardness than the hardness of a soft material forming the optic portion.

Figure 5A:
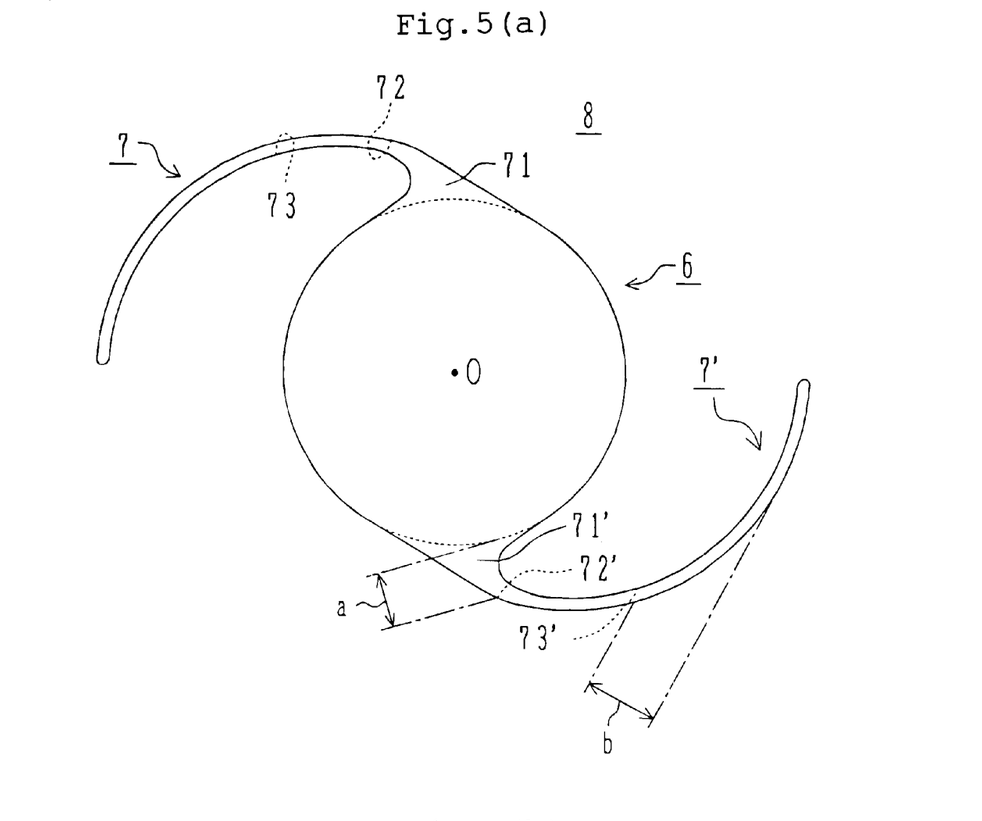
FIG. 5(a) is a front view of one example of the soft intraocular lens (intraocular lens 2) of the present invention.
Figure 5B:
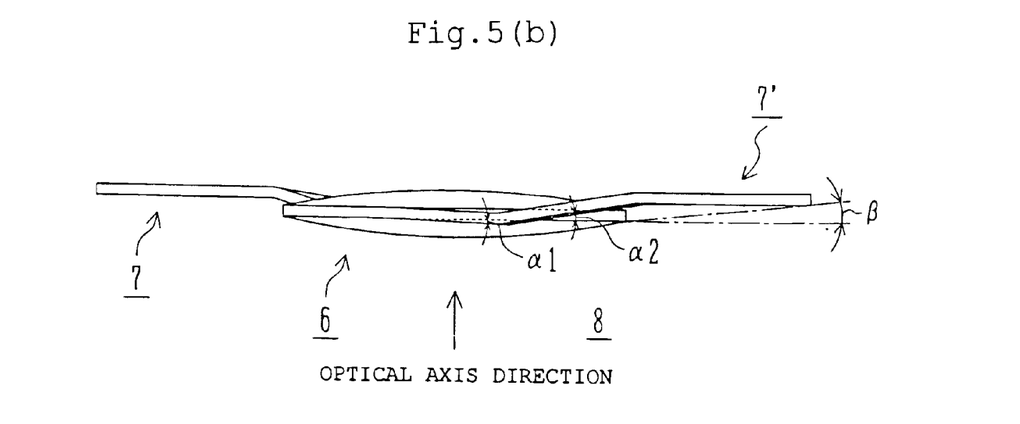
FIG. 5(b) is a side view of the same.
Figure 6:
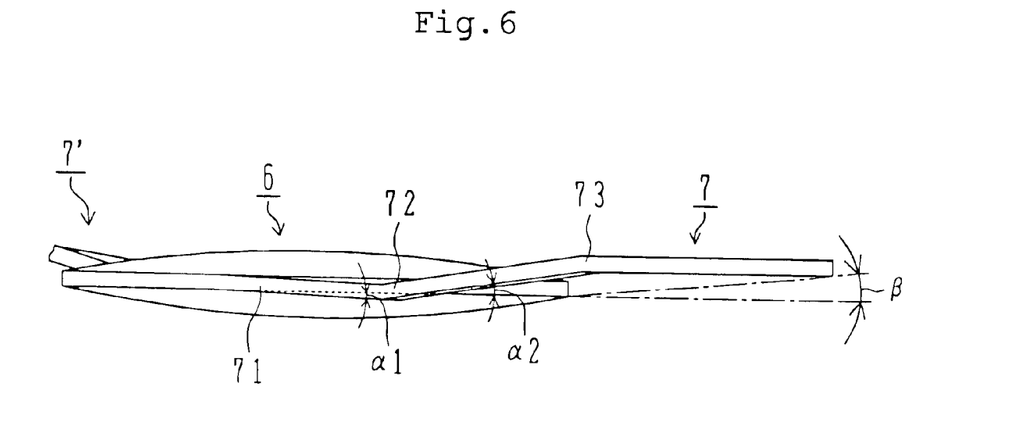
FIG. 6 is an enlarged view of part shown in FIG. 5(b).

FIGS. 5(*a*) and 5(*b*) show an example of configuration of the soft intraocular lens (intraocular lens 2) of the present invention. FIG. 5(*a*) is a plan view of the same, FIG. 5(*b*) is a side view of the same, and FIG. 6 is an enlarged view of part shown in FIG. 5(*b*).

In FIGS. 5(*a*) and 5(*b*), the soft intraocular lens is a one-piece soft intraocular lens 8 having an optic portion 6 and an arm-like haptic portion 7,7' extending outwardly from circumferential portions of the optic portion 6, the optic and haptic portions being integrally formed.

The optic portion 6 is a circular convex lens formed of a soft optic portion material to be described later and has an outer diameter of approximately 5.0 to 6.5 mm.

The haptic portion 7,7' is formed of PMMA and formed of two arm-like members extending from two sites which are on circumferential portions of the optic portion 6 and have a central point symmetrical relationship with regard to the center O of the optic portion 6. As shown in FIG. 5(*a*), the haptic portion 7,7' when viewed as a plan view has a curved form which extends outwardly from a start portion 71,71' located in a boundary formed with the optic portion 6 while decreasing the ratio of clearance from the optic portion and which therefore nearly forms a concentric circle with the optic portion in the vicinity of its end portion.

In the form of the haptic portion 7,7' when viewed as a side view, as shown in FIG. 5(*b*) and FIG. 6, the haptic portion 7,7' extends outwardly from a base of the start portion 71,71' and forms an angle $\alpha_1$ with a plane at right angles with the optical axis of the optic portion 6, a first bendable portion 72,72' is formed at a distance "a" from the base, and a second bendable portion 73,73' is formed at a distance "b" from a tangent line on a site which is near the top portion thereof and has a nearly concentric circle relationship with the optic portion 6. That portion of the haptic portion 7,7' which is positioned outside the second bendable portion 73,73' is formed so as to be nearly in parallel with a plane at right angles with the optical axis.

The above distance "a" preferably set at 3 mm or less. The above angle $\alpha_1$ is preferably set at 12 degrees or less. The distance "b" is generally set at several millimeters. Further, the bending angle of the first bendable portion 72,72' is set such that the portion located between the first bendable portion 72,72' and the second bendable portion 73,73' forms an angle of $\alpha_2$ with a plane in perpendicular with the above optical axis. The bending angle of the second bendable portion is set at such an angle that the portion located outside the second bendable portion 73,73' is nearly in parallel with a plane at right angles with the optical axis. When a straight line formed by connecting the top end of the haptic portion 7,7' and a circumferential end portion of the optic portion forms an angle $\beta$ with a plane at right angles with the above optical axis, the above $\alpha_2$ is preferably set such that the above $\beta$ is approximately 5 degrees.

The above-structured one-piece soft intraocular lens can be produced in the same manner as in the production of the one-piece intraocular lens (intraocular lens 1) of the present invention.

The present invention will be explained in detail with reference to Examples, while the present invention shall not be limited by these Examples.

EXAMPLE 1

A monomer mixture for forming an optic portion was prepared by mixing

| | |
|---|---|
| 2-phenylethyl methacrylate (PEMA) | 56 parts by weight |
| n-butyl acrylate (BA) | 35 parts by weight |
| 2-[2-(perfluorooctyl)ethoxy-1-methylethyl methacrylate (BRM) | 9 parts by weight |
| ethylene glycol dimethacrylate (EDMA) and | 3 parts by weight |
| azobisisobutyronitrile (AIBN) | 0.3 part by weight. |

There was provided a disc which had a cylindrical concave portion having a diameter of 6.2 mm and had a diameter of 16 mm and a thickness of approximately 5 mm as shown in FIG. 1 and which was formed of PMMA. The above monomer mixture was charged in the concave portion of the above disc and polymerized under pressure at a nitrogen pressure of 2.0 kg/cm² at a temperature of 60° C. for 2 hours, and then, the polymerized product was maintained at 80° C. for 2 hours and then at 100° C. for 2 hours to complete the polymerization.

Then, a 3 mm thick disc was taken by cutting, and an optical surface was cut with blowing cold air of −5° C. to the disc. With blowing cold air again, the disc was cut with a milling machine as shown in FIG. 3, and while cold air was blown to the surface opposite to the surface cut with the milling machine, the optical surface was cut. In this case, a hopper-shaped haptic portion was formed.

The so-obtained lens was barrel-polished in a constant-temperature chamber at −5° C. for 3 days, to give a one-piece intraocular lens shown in FIG. 4.

Table 1 shows the appearance, the self-adhesion, the form restoration-capability and the refractive index of the above one-piece intraocular lens.

EXAMPLES 2–8

One-piece intraocular lenses were prepared in the same manner as in Example 1 except that the monomer mixture for forming an optic portion was changed as shown in FIGS. 1 or 2.

Tables 1 and 2 show the appearance, the self-adhesion, the form restoration capability and the refractive index of the above one-piece intraocular lenses.

TABLE 1

| | Example | | | |
|---|---|---|---|---|
| | 1 | 2 | 3 | 4 |
| Composition of monomer mixture (wt %) | | | | |
| BRM 1) | 9 | 7 | 8 | 8 |
| PEMA 2) | 56 | 50 | 62 | 46 |
| BA 3) | 35 | 43 | 30 | 46 |

TABLE 1-continued

| | Example | | | |
|---|---|---|---|---|
| | 1 | 2 | 3 | 4 |
| ERA 4) | — | — | — | — |
| CHMP 5) | — | 0.5 | 0.5 | 0.5 |
| EDMA 6) | 3 | 3 | 3 | 3 |
| AIBN 7) | 0.3 | 0.3 | 0.3 | 0.3 |
| Appearance | Transparent | Transparent | Transparent | Transparent |
| Self-adhesion 8) | Nil | Nil | Nil | Nil |
| Form restoration capability 9) (second) | 45 | 28 | 52 | 25 |
| Refractive index 10) | 1.512 | 1.506 | 1.520 | 1.504 |

TABLE 2

| | Example | | | |
|---|---|---|---|---|
| | 5 | 6 | 7 | 8 |
| Composition of monomer mixture (wt %) | | | | |
| BRM 1) | 10 | 10 | 8 | 15 |
| PEMA 2) | 49 | 50 | 55 | 47 |
| BA 3) | 41 | — | — | — |
| ERA 4) | — | 40 | 37 | 38 |
| CHMP 5) | 0.5 | 0.5 | 0.5 | 0.5 |
| EDMA 6) | 3 | 3 | 3 | 3 |
| AIBN 7) | 0.3 | 0.3 | 0.3 | 0.3 |
| Appearance | Transparent | Transparent | Transparent | Transparent |
| Self-adhesion 8) | Nil | Nil | Nil | Nil |
| Form restoration capability 9) (second) | 33 | 35 | 48 | 37 |
| Refractive index 10) | 1.502 | 1.504 | 1.510 | 1.497 |

Notes to Tables 1 and 2:
1) BRM: 2-[2-(perfluorooctyl)ethoxy]-1-methylethyl methacrylate
2) PEMA: 2-phenylethyl methacrylate
3) BA: n-butyl acrylate
4) EHA: 2-ethylhexyl acrylate
5) CHMP: 5-chloro-2-[2-hydroxy-5-(β-methacryloyl-oxyethylcarbamoyloxyethyl)]phenyl-2H-benzotriazole
6) EDMA: ethylene glycol dimethacrylate
7) AIBN: azobisisobutyronitrile
8) Self-adhesion: The optic portion of an intraocular lens was bent with an intraocular lens bending nipper, and the optic portion did not show self-adhesion when released was taken as no-adhesion.
9) Form restoration capability: The optic portion of an intraocular lens was bent with an intraocular lens bending nipper, and a time taken until the optic portion restored its original diameter was used.
10) Refractive index: An intraocular lens was measured for a refractive index with e-ray (546.1 nm) at 36° C. with a refractometer supplied by Atago Co.

EXAMPLE 9

A monomer mixture for forming an optic portion was prepared by mixing

| | |
|---|---|
| n-butyl acrylate | 42 parts by weight |
| phenyl ethyl methacrylate | 49 parts by weight |
| perfluorooctylethyloxypropylene methacrylate | 9 parts by weight |
| ethylene glycol dimethacrylate and | 3 parts by weight |
| azobisisobytyronitrile | 0.3 part by weight. |

There was provided a disc which had a cylindrical concave portion having a diameter of 6.5 mm and had a diameter of 16.5 mm and a thickness of approximately 5 mm as shown in FIG. 1 and which was formed of PMMA. The above monomer mixture was charged in the concave portion of the above disc and polymerized under pressure at a nitrogen pressure of 2.0 kg/cm$^2$ at a temperature of 60° C. for 2 hours, and then, the polymerized product was maintained at 80° C. for 2 hours and then at 100° C. for 2 hours to complete the polymerization.

Then, a 3 mm thick disc was taken by cutting, and an optical surface was cut with blowing cold air of −10° C. to the disc. With blowing cold air again, the disc was cut in the form of one piece with a milling machine as shown in FIG. 3, whereby a lens having a predetermined optic portion form and a predetermined haptic portion form were obtained.

The so-obtained lens was barrel-polished for 5 days, to give a one-piece intraocular lens shown in FIGS. 5 and 6.

The distance "a" was 1 mm, the angle $\alpha_1$ was approximately 5 degrees, the distance "b" was 1.5 mm, and the angle $\alpha_2$ was approximately 17 degrees.

EXAMPLE 10

A one-piece soft intraocular lens was obtained in the same manner as in Example 9 except that the angle $\alpha_1$ was changed to approximately 10 degrees and that the angle $\alpha_2$ was changed to approximately 29 degrees.

COMPARATIVE EXAMPLE 1

A one-piece soft intraocular lens was obtained in the same manner as in Example 9 except that the form of a haptic portion was changed to a conventional type as shown in FIG. 8 and that α was set at 5 degrees.

COMPARATIVE EXAMPLE 2

A one-piece soft intraocular lens was obtained in the same manner as in Example 9 except that the form of a haptic portion was changed to a conventional wing type as shown in FIG. 9 and that a was set at 10 degrees.

COMPARATIVE EXAMPLE 3

A one-piece intraocular lens having an optic portion and a haptic portion which were integrally formed of PMMA and whose haptic portion had a conventional form (α=5 degrees) as shown in FIG. 8 was used as Comparative Example 3.

COMPARATIVE EXAMPLE 4

A one-piece intraocular lens having an optic portion and a haptic portion which were integrally formed of PMMA and whose haptic portion had a conventional wing type form (α=10 degrees) as shown in FIG. 9 was used as

COMPARATIVE EXAMPLE 4.

The intraocular lenses in Examples 9 and 10 and Comparative Examples 1 to 4 were tested as follows.

(1) Resolution/Power Test

A lens was fixed in a ring having a diameter of 10 mm and measured for a resolution and a power (lens strength).

The results of the above measurement were as follows. Each of the intraocular lenses in Examples 9 and 10 and Comparative Examples 3 and 4 was fit in the ring having a diameter of 10 mm, and it was found that these lenses had a resolution and a power as designed. In the intraocular lenses obtained in Comparative Examples 1 and 2, however, the optic portion was deformed since the optic portion gradually floated after the lens was fixed in the ring having a diameter of 10 mm. Therefore, the lenses in Comparative Examples 1 and 2 were not measurable for a resolution and a power in the ring having a diameter of 10 mm.

(2) Holding Test Under Compression

Figure 10:
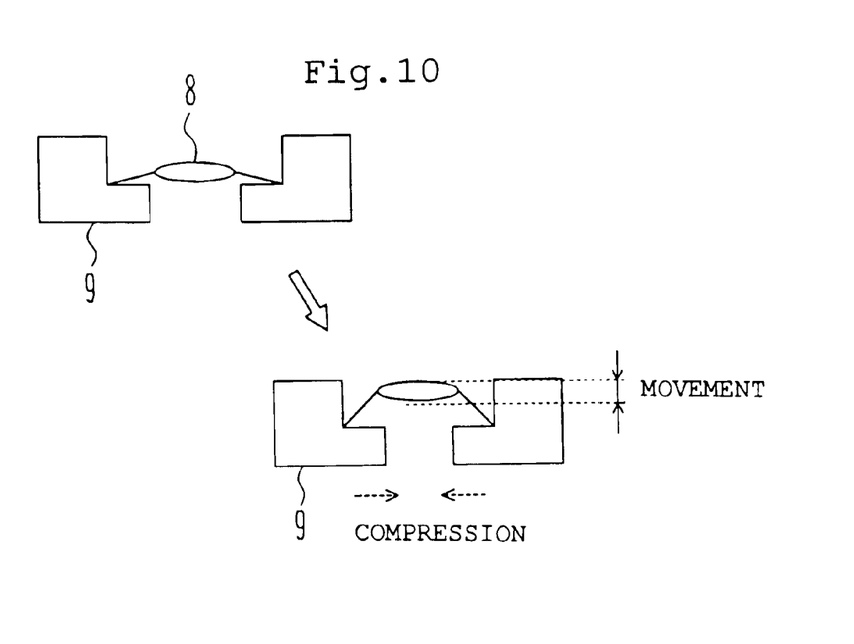
FIG. 10 shows how a compression holding test is carried out.

As shown in FIG. 10, a lens 8 was set in a tool 9 whose holding diameter was variable, and the lens was compressed by decreasing the holding diameter of the tool 9 to 11 mm and to 10 mm. In this case, the optic portion was measured for a distance of movement of the center of the optic portion in the optical axis direction with a digital measuring microscope (STM 5-322, supplied by Olympus Optical Co., Ltd.).

Figure 11:
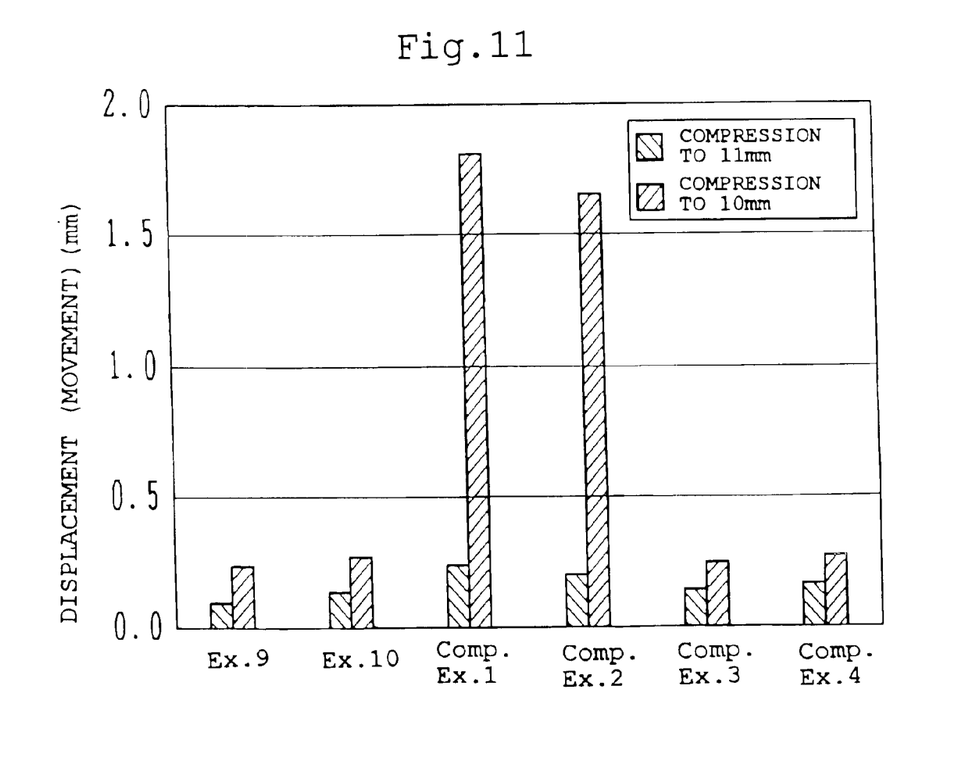
FIG. 11 shows results of a compression holding test.

The results of the above holding test under compression were as shown in FIG. 11. As shown in FIG. 11, the intraocular lenses in Examples 9 and 10 showed almost no difference at any time of the compression to a diameter of 11 mm and the compression to a diameter of 10 mm and were remarkably excellent when compared with the conventional one-piece type lens (α=5 degrees) formed of PMMA (optic portion was also formed of PMMA—hard material) shown in FIG. 8 and the wing type lens (α=10 degrees) shown in FIG. 9 (Comparative Examples 3 and 4).

However, the lens having an optic portion formed of the soft material and a haptic portion shown in FIG. 8 (α=5 degrees) and the lens having an optic portion formed of the soft material and a wing type haptic portion shown in FIG. 9 (α=10 degrees), i.e., the lenses in Comparative Examples 1 and 2, showed a large movement of their optic portions in the optical axis direction and suffered deformation when compressed to a diameter of 10 mm.

Figure 12A:
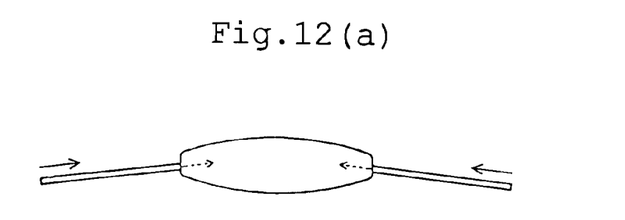
FIG. 12(a) shows the effect of compressive force exerted on the haptic portion of a conventional lens having an optic portion formed of a soft material.

The above results are obtained presumably due to the following function. That is, in the conventional type lens shown in FIG. 8, whose optic portion is formed of a soft material, as shown in FIG. 12(a), the compressive force exerted on the haptic portion is directly transmitted in the longitudinal direction of the haptic portion to reach the optic portion and causes the optic portion to rise in the optical axis direction or deforms the optic portion.

Figure 12B:
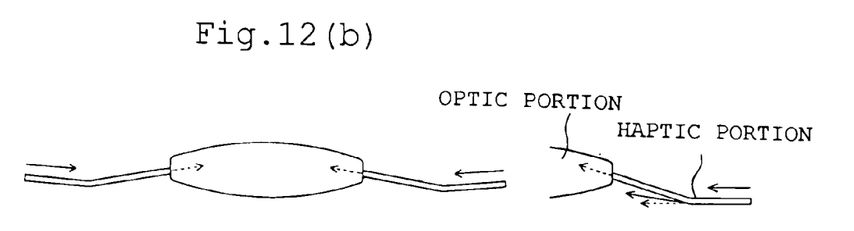
FIG. 12(b) shows the effect in a conventional lens of compressive force exerted on an optic portion of a soft material and partial dispersion from the optic portion.

In the conventional wing type lens shown in FIG. 9, whose optic portion is formed of a soft material, as shown in FIG. 12(b), the compressive force exerted on the haptic portion is once dispersed, but a major part of the compressive force is transmitted to the optic portion since the dispersion is insufficient, and it causes the optic portion to rise in the optical axis direction or deforms the optic portion.

Figure 12C:
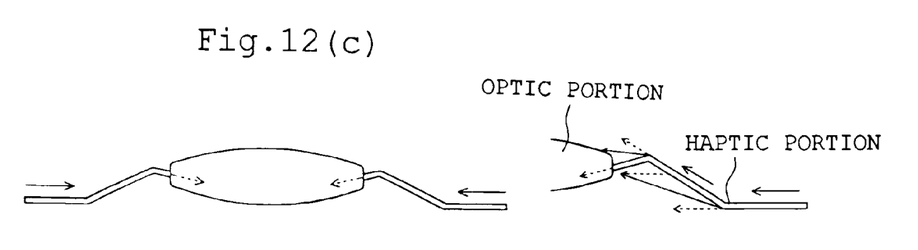
FIG. 12(c) shows in lenses according to the present invention compressive force is dispersed at least twice before reaching the optic portion.

In contrast, in the lenses obtained in Examples of the present invention, as shown in FIG. 12(c), the compressive force is dispersed twice before it reaches the optic portion and the force to be exerted on the optic portion is moderated.

Industrial Utility

In the intraocular lens (intraocular lens 1) of the present invention, the optic portion is soft, and when it is bent and then released, the optic portion does not undergo self adhesion and restores its original shape in 20 to 60 seconds. Therefore, there is produced an effect that the intraocular lens of the present invention is free from damaging a capsule after inserted in an eye.

According to the process of the present invention, further, it is not required to provide the step of hydrating the optic portion, nor is it required to provide the step of esterification, after a one-piece intraocular lens is produced. The angle of the haptic portion can be therefore maintained, and one-piece intraocular lenses having hard and strong haptic portions can be highly efficiently produced without a variability in product quality in simple steps.

According to the process of the present invention, further, the one-piece intraocular lens can be produced in the same method as that employed in the production of conventional one-piece types by only cooling in cutting and polishing steps.

Further, the soft intraocular lens (intraocular lens 2) of the present invention has a characteristic feature in that the intraocular lens has a haptic portion provided with a bendable portion which, when a compressive force is externally exerted on the haptic portion so as to move at least any site of the haptic portion toward the optic portion, can absorb at least part of the external compressive force by deformation and decreases the force to be transmitted to the optic portion. As a result, when a capsule shrinks after the above soft intraocular lens is inserted in the capsule, the optic portion undergoes neither deformation nor distortion.

What is claimed is:

1. A one piece intraocular lens having an optic portion which functions as a substitute lens for a crystalline lens and a haptic portion for fixing and holding the optic portion in a predetermined position in an eye, the optic portion having an optical axis and being formed of a copolymer obtained by polymerization of a monomer mixture containing

(a) 5 to 20% by weight of 2-[2-(perfluorooctyl)ethoxy]-1-methylethyl (meth)acrylate of the formula (I), (I)

wherein $R^1$ is hydrogen or methyl,

(b) 40 to 70% by weight of 2-phenylethyl (meth)acrylate of the formula (II), (II)

wherein $R^2$ is hydrogen or methyl, (c) 25 to 50% by weight of alkyl (meth)acrylate of the formula (III)

(III)

wherein $R^3$ is hydrogen or methyl and $R^4$ is a $C_4$–$C_{12}$ linear, branched or cyclic alkyl group, and (d) 0.5 to 5% by weight, based on the total amount of the components (a) to (c), of a crosslinking monomer, the haptic portion is formed of polymethyl methacrylate and has a first angle with a plane at right angles with the optical axis of the optic portion and through an optical center of the lens as the haptic portion extends outwardly from its start portion in the vicinity of the optic portion, and the haptic portion has a first bendable portion which is bent so as to form a second angle, an angle opposite to the first angle, with said plane in a position located outside the start portion of the haptic portion and a second bendable portion which is bent so as to form a third angle, an angle opposite to the second angle, with said plane in a position located outside the first bendable portion, wherein at least the first and second bendable portions of the haptic portion from a proximal end to a distal end extend radially farther away from the optical center of the lens.

2. The one-piece intraocular lens of claim 1, wherein the optic portion has deformable softness.

3. The one-piece intraocular lens of claim 1, wherein the optic portion and the haptic portion have a junction portion formed of an interpenetrating network structure.

4. A process for the production of a one-piece intraocular lens having an optic portion which functions as a substitute lens for a crystalline lens and a haptic portion for fixing and holding the optic portion in a predetermined position in an eye, the optic portion having an optical axis, wherein the haptic portion has a first angle with a plane at right angles with the optical axis of the optic portion and through an optical center of the lens as the haptic portion extends outwardly from its start portion in the vicinity of the optic portion, and the haptic portion has a first bendable portion which is bent so as to form a second angle, an angle opposite to the first angle, with said plane in a position located outside the start portion of the haptic portion and a second bendable portion which is bent so as to form a third angle, an angle opposite to the second angle, with said plane in a position located outside the first bendable portion, wherein at least the first and second bendable portions of the haptic portion from a proximal end to a distal end extend radially farther away from the optical center of the lens, the process comprising polymerizing an optic-portion-forming monomer mixture containing:

(a) 5 to 20% by weight of 2-[2-(perfluorooctyl)ethoxy]-1-methylethyl (meth)acrylate of the formula (I), (I)

wherein $R^1$ hydrogen or methyl,

(b) 40 to 70% by weight of 2-phenylethyl (meth)acrylate of the formula (II), (II)

wherein $R^2$ is hydrogen or methyl, (c) 25 to 50% by weight of alkyl (meth)acrylate of the formula (III)

(III)

wherein $R^3$ is hydrogen or methyl and $R^4$ is a $C_4$–$C_{12}$ linear, branched or cyclic alkyl group, and (d) 0.5 to 5% by weight, based on the total amount of the components (a) to (c), of a crosslinking monomer, while keeping the monomer mixture in contact with a haptic-portion-forming material containing polymethyl methacrylate, or polymerizing a haptic-portion-forming monomer containing methyl methacrylate while keeping the haptic-portion-forming monomer in contact with an optic-portion-forming material formed of a copolymer obtained by polymerization of the above monomer mixture, to integrate the optic-portion-forming material and the haptic-portion-forming material, and thereafter cutting and polishing the integrated product.

5. The process of claim 4, wherein a disc which is formed of polymethyl methacrylate and has a cylindrical concave portion having predetermined dimensions is provided and the monomer mixture is charged in the cylindrical concave portion and polymerized.

6. The process of claim 4, wherein the cutting and polishing are carried out with cooling.

7. A soft intraocular lens having an optic portion formed of a deformable soft material which functions as a substitute lens for a crystalline lens and a haptic portion which is formed of arm members extending outwardly from circumferential portions of the optic portion and is for fixing and holding the optic portion in a predetermined position in an eye, the optic portion having an optical axis, wherein the haptic portion has a first angle with a plane at right angles with the optical axis of the optic portion and through an optical center of the lens as the haptic portion extends outwardly from its start portion in the vicinity of the optic portion, and the haptic portion has a first bendable portion which is bent so as to form a second angle, an angle opposite to the first angle, with said plane in a position located outside the start portion of the haptic portion and a second bendable portion which is bent so as to form a third angle, an angle opposite to the second angle, with said plane in a position located outside the first bendable portion, wherein at least the first and the second bendable portions of the haptic portion from a proximal end to a distal end extend radially farther away from the optical center of the lens, and when a compressive force is externally exerted on the haptic portion so as to move at least any site of the haptic portion toward the optic portion, the haptic portion can absorb at least part of the external compressive force by deformation which decreases the force to be transmitted to the optic portion.

8. The soft intraocular lens of claim 7, wherein when force is applied to the lens and transmitted to the optic portion to move the optic portion in a direction in parallel with an optical axis of the optic portion, the bendable portion deforms and absorbs at least part of the applied force.

9. The soft intraocular lens of claim 7, wherein the first angle is 12 degrees or less.

10. The soft intraocular lens of claim 7, wherein the distance from the start portion of the haptic portion to the first bendable portion is 3 mm or less.

11. The soft intraocular lens of claim 7, wherein the optic portion and the haptic portion are integrally formed.

12. The soft intraocular lens of claim 7, wherein the haptic portion is formed of a hard material having a higher hardness than a soft material forming the optic portion.

13. A soft intraocular lens having an optic portion formed of a deformable soft material which functions as a substitute lens for a crystalline lens and a haptic portion which is formed of arm members extending outwardly from circumferential portions of the optic portion and is for fixing and holding the optic portion in a predetermined position in an eye, the optic portion having an optical axis, wherein the haptic portion has a first angle with a plane which passes a start portion of the haptic portion and which is in the direction at right angles with the optical axis of the optic portion, the haptic portion extending outwardly from the start portion in the vicinity of the optic portion, and the haptic portion has a first bendable portion which is bent so as to form a second angle, an angle opposite to the first angle, with said plane in a position located outside the start portion of the haptic portion and a second bendable portion which is bent so as to form a third angle, an angle opposite to the second angle, with said plane in a position located outside the first bendable portion, the haptic portion thus crossing an imaginary line parallel to said plane and extending through an optical center of the lens, wherein each bendable portion of the haptic portion extends away from the optical center of the lens, and when a compressive force is externally exerted on the haptic portion so as to move at least any site of the haptic portion toward the optic portion, the haptic portion can absorb at least part of the external compressive force by deformation which decreases the force to be transmitted to the optic portion.

14. The soft intraocular lens of claim 13, wherein the optic portion is formed of a copolymer obtained by polymerization of a monomer mixture containing

(a) 5 to 20% by weight of 2-[2-(perfluorooctyl)ethoxy]-1-methylethyl (meth)acrylate of the formula (I), (I)

wherein $R^1$ is hydrogen or methyl,

(b) 40 to 70% by weight of 2-phenylethyl (meth)acrylate of the formula (II), (II)

wherein $R^2$ is hydrogen or methyl, (c) 25 to 50% by weight of alkyl (meth)acrylate of the formula (III)

(III)

wherein $R^3$ is hydrogen or methyl and $R^4$ is a $C_4$–$C_{12}$ linear, branched or cyclic alkyl group, and (d) 0.5 to 5% by weight, based on the total amount of the components (a) to (c), of a crosslinking monomer.

15. The soft intraocular lens of claim 13 wherein the first angle is 12 degrees or less.

16. The soft intraocular lens of claim 13, wherein the distance from the start portion of the haptic portion to the first bendable portion is 3 mm or less.

17. The soft intraocular lens of claim 13, wherein the optic portion and the haptic portion are integrally formed.

18. The soft intraocular lens of claim 13, wherein the haptic portion is formed of a hard material having a higher hardness than a soft material forming the optic portion.

19. The process of claim 4, wherein the haptic-portion-forming material is pressed before the monomer mixture is brought into contact with the haptic-portion-forming material.

20. A process for the production of a one-piece intraocular lens having an optic portion which functions as a substitute lens for a crystalline lens and a haptic portion for fixing and holding the optic portion in a predetermined position in an eye, the optic portion having an optical axis, the process comprising polymerizing an optic-portion-forming monomer mixture containing:

(a) 5 to 20% by weight of 2-[2-(perfluorooctyl)ethoxy]-1-methylethyl (meth)acrylate of the formula (I), wherein $R^1$ hydrogen or methyl, (b) 40 to 70% by weight of 2-phenylethyl (meth)acrylate of the formula (II), wherein $R^2$ is hydrogen or methyl, (c) 25 to 50% by weight of alkyl (meth)acrylate of the formula (III)

wherein $R^3$ is hydrogen or methyl and $R^4$ is a $C_4$–$C_{12}$ linear, branched or cyclic alkyl group, and (d) 0.5 to 5% by weight, based on the total amount of the components (a) to (c), of a crosslinking monomer, while keeping the monomer mixture in contact with a haptic-portion-forming material containing polymethyl methacrylate, or polymerizing a haptic-portion-forming monomer containing methyl methacrylate while keeping the haptic-portion-forming monomer in contact with an optic-portion-forming material formed of a copolymer obtained by polymerization of the above monomer mixture, to integrate the optic-portion-forming material and the haptic-portion-forming material, and thereafter cutting and polishing the integrated product wherein the haptic portion has a first angle with a plane which passes a start portion of the haptic portion and which is in the direction at right angles with the optical axis of the optic portion, the haptic portion extending outwardly from the start portion in the vicinity of the optic portion, and the haptic portion has a first bendable portion which is bent so as to form a second angle, an angle opposite to the first angle, with said plane in a position located outside the start portion of the haptic portion and a second bendable portion which is bent so as to form a third angle, an angle opposite to the second angle, with said plane in a position located outside the first bendable portion, the haptic portion thus crossing an imaginary line parallel to said plane and extending through an optical center of the lens, wherein each bendable portion of the haptic portion extends away from the optical center of the lens, and when a compressive force is externally exerted on the haptic portion so as to move at least any site of the haptic portion toward the optic portion, the haptic portion can absorb at least part of the external compressive force by deformation which decreases the force to be transmitted to the optic portion.

21. A soft intraocular lens having an optic portion formed of a deformable soft material which functions as a substitute lens for a crystalline lens and a haptic portion which is formed of arm members extending outwardly from circumferential portions of the optic portion and is for fixing and holding the optic portion in a predetermined position in an eye, the optic portion having an optical axis, wherein the haptic portion has a first angle with a plane which passes a start portion of the haptic portion and which is in the direction at right angles with the optical axis of the optic portion, the haptic portion extending outwardly from the start portion in the vicinity of the optic portion, and the haptic portion has a first bendable portion which is bent so as to form a second angle, an angle opposite to the first angle, with said plane in a position located outside the start portion of the haptic portion and a second bendable portion which is bent so as to form a third angle, an angle opposite to the second angle, with said plane in a position located outside the first bendable portion, the haptic portion thus crossing an imaginary line parallel to said plane and extending through an optical center of the lens, wherein each bendable portion of the haptic portion extends away from the optical center of the lens, and wherein that portion of each haptic portion which is positioned outside the second bendable portion is formed so as to be nearly in parallel with a plane at right angles with the optical axis, and when a compressive force is externally exerted on the haptic portion so as to move at least any site of the haptic portion toward the optic portion, the haptic portion can absorb at least part of the external compressive force by deformation which decreases the force to be transmitted to the optic portion.

22. A The soft intraocular lens of claim 21, wherein the optic portion has deformable hardness.

23. The soft intraocular lens of claim 21, wherein the first angle is 12 degrees or less.

24. The soft intraocular lens of claim 21, wherein the distance from the start portion of the haptic portion to the first bendable portion is 3 mm or less.

25. The soft intraocular lens of claim 21, wherein the optic portion and the haptic portion are integrally formed.

26. The soft intraocular lens of claim 21, wherein the haptic portion is formed of a hard material having a higher hardness than a soft material forming the optic portion.

* * * * *